US009655609B2

(12) United States Patent
Rizk et al.

(10) Patent No.: US 9,655,609 B2
(45) Date of Patent: May 23, 2017

(54) SOFT SUTURE ANCHOR (71) Applicant: Tepha, Inc., Lexington, MA (US)

(72) Inventors: Said Rizk, Windham, NH (US); David P. Martin, Arlington, MA (US); Matthew Bernasconi, Norwood, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 1 day.

(21) Appl. No.: 14/328,210

(22) Filed: Jul. 10, 2014

(65) Prior Publication Data
US 2015/0018878 A1 Jan. 15, 2015

Related U.S. Application Data (60) Provisional application No. 61/844,479, filed on Jul. 10, 2013, provisional application No. 61/986,695, filed on Apr. 30, 2014.

(51) Int. Cl.
*A61B 17/04* (2006.01)
*B29C 47/00* (2006.01)
*A61L 31/12* (2006.01)

(52) U.S. Cl.
CPC ........ *A61B 17/0401* (2013.01); *A61L 31/127* (2013.01); *A61L 31/128* (2013.01); *B29C 47/0038* (2013.01); *A61B 2017/044* (2013.01); *A61B 2017/0445* (2013.01); *A61B 2017/0464* (2013.01)

(58) Field of Classification Search
CPC ............ A61B 17/0401; A61B 17/0466; A61B 2017/0414; A61B 2017/042; A61B 2017/0422; A61B 2017/0424; A61B 2017/0445; A61B 2017/0464; A61B 2017/0088; A61L 27/10; A61L 31/026
USPC ........................................ 606/232
See application file for complete search history.

(56) References Cited

U.S. PATENT DOCUMENTS

| 5,527,341 | A | * | 6/1996 | Gogolewski | ....... A61B 17/0401 606/148 |
| 5,584,836 | A | * | 12/1996 | Ballintyn | ........... A61B 17/0401 606/232 |
| 5,717,717 | A | | 2/1998 | Yang | |
| 6,838,493 | B2 | | 1/2005 | Williams | |
| 2004/0049194 | A1 | * | 3/2004 | Harvie | ............... A61B 17/8836 606/232 |
| 2006/0293674 | A1 | * | 12/2006 | Li | ....................... A61B 17/0401 606/273 |
| 2011/0071551 | A1 | * | 3/2011 | Singhatat | ........... A61B 17/0401 606/145 |
| 2011/0098727 | A1 | | 4/2011 | Kaiser | |

(Continued)

FOREIGN PATENT DOCUMENTS

WO 2011119742 9/2011
WO 2013050775 4/2013

*Primary Examiner* — Todd J Scherbel
(74) *Attorney, Agent, or Firm* — Pabst Patent Group LLP (57) ABSTRACT Compositions and materials for making soft suture anchors comprising materials that improve osteointegration have been developed. These compositions and materials comprise bioceramics, resorbable materials, and combinations thereof. A preferred embodiment comprises a soft suture anchor comprising a resorbable ceramic and a resorbable suture.

20 Claims, 3 Drawing Sheets (56) References Cited

U.S. PATENT DOCUMENTS

| | | | |
|---|---|---|---|
| 2012/0053627 A1* | 3/2012 | Sojka | A61B 17/0401 |
| | | | 606/232 |
| 2012/0290004 A1 | 11/2012 | Lombardo | |
| 2013/0018416 A1 | 1/2013 | Lombardo | |
| 2013/0131722 A1 | 5/2013 | Marchand | |
| 2013/0238027 A1* | 9/2013 | Zhang | A61B 17/00491 |
| | | | 606/232 |

* cited by examiner

FIG. 1A Cross-Section

FIG. 1B Assembly

SOFT SUTURE ANCHOR

CROSS-REFERENCE TO RELATED APPLICATIONS

This application claims the benefit of priority to U.S. Ser. No. 61/844,479, filed on Jul. 10, 2013, and U.S. Ser. No. 61/986,695 filed on Apr. 30, 2014, the disclosure of which incorporated herein by reference.

FIELD OF THE INVENTION

The present invention generally relates to compositions and implants comprising polymers and bioceramics that can be used in many types of soft suture anchors for fixation applications including soft tissue to bone and bone to bone.

BACKGROUND OF THE INVENTION

Suture anchors are commonly used in surgery to fix soft tissues, such as ligaments and tendons, to bone. The anchor component, which is inserted into bone, may be made from metal or a polymer, and is typically implanted into a pre-drilled hole. Anchor designs in current use include those that screw into the bone, and molded parts that engage with the bone using an interference fit. The anchor design normally includes an eyelet, for example, a hole or a loop in the anchor, through which the suture can be passed, to allow attachment of the suture to the anchor. The suture may be made from a non-absorbable material or an absorbable material, and may also be a monofilament, braid or combinations thereof. Once the anchor has been inserted into the bone, the suture can be used to fix soft tissue to the bone.

U.S. Pat. No. 6,838,493 to Williams et al., for example, discloses suture anchors made from resorbable polyhydroxyalkanoates and other materials, including poly-4-hydroxybutyrate, wherein the anchor component is a rigid molded part that either screws into the bone or engages using an interference fit.

Very recently, soft suture anchors have been developed, for example, the Biomet JUGGERKNOT™, Stryker ICONIX™, ConMed LINVATEC® Y-knot, and Smith & Nephew SUTUREFIX ULTRA® devices, to eliminate concerns with existing suture anchor technology. During deployment, these soft suture anchors are inserted into pre-drilled pilot holes, the suture anchor mechanisms are released, and the anchors are fixed securely in the bone holes.

Various designs have been used to secure soft suture anchors in bone, including expansion of braided suture, vertical contraction and lateral expansion of suture tapes, and the use of a sheath that bunches inside the bone hole causing targeted compression. US Patent Application No. 2011/0098727 to Kaiser et al. discloses a flexible anchor made from a braided or woven fabric with two openings positioned between the first and second ends of the flexible anchor such that one end of a suture can be passed inside the first opening of the flexible anchor, along a passageway inside the flexible anchor, and out of the second opening in the flexible anchor. The ends of the suture can be held so that the flexible anchor forms substantially a U-shape for insertion, with the ends of the flexible anchor forming legs or tail portions that can provide additional resistance when the anchor is inserted into bone and tension is placed on the suture. The tension on the suture causes the mid-section of the flexible anchor to rise, bunch, and compress into the cancellous bone to secure the anchor.

U.S. Patent Application No. 2013/0131722 to Marchand et al. discloses a soft suture anchor wherein the free ends of the suture enter and exit a sleeve member, and the suture passes one or more times through the interior and exterior of the sleeve member. The sleeve member is substantially hollow, and is formed by braiding. Marchand et al. disclose the use of surface coatings of hydroxyapatite powder or tricalcium phosphate on the sleeve to allow bone ingrowth. U.S. Patent Application No. 2012/0290004 to Lombardo et al. discloses a soft suture anchor comprising a fibrous construct and at least one suture, wherein the suture passes through the fibrous construct in at least three locations. U.S. Patent Application No. 2013/0018416 to Lombardo et al. discloses soft suture anchors made of braided or monofilament suture.

Smith and Nephew (Mass. USA) recently launched the SUTUREFIX ULTRA® device, which allows the soft anchor to form a ball against the inserter tube rather than the cortical layer of bone. However, the anchor still deploys laterally in a pre-drilled hole, forming a ball that provides sufficient compression for fixation (see: Smith & Nephew, Suturefix Ultra Brochure 00496 V 1, March 2014).

The soft suture anchors offer a number of advantages over conventional suture anchors. They are designed to reduce or eliminate bone loss following implantation, and can often be inserted into smaller bone holes minimizing damage to healthy tissue. The soft suture anchors also eliminate any hardware related issues by replacing the anchor component with a soft strand of suture material and a braid or a combination of a suture strand and a surrounding sleeve. Importantly, the soft suture anchors eliminate the possibility of loose pieces of anchor material getting into the joint if there is any breakage of the anchor.

To further improve the performance of soft suture anchors, it would be desirable to identify materials that can be used to improve the osteointegration of soft suture anchors. It would also be desirable to identify soft suture anchors where at least the anchor component is made from a resorbable composition that improves osteointegration, and more particularly where the anchor is completely replaced by bone following implantation. In addition, it would be desirable to identify a range of compositions such that the resorption rate of the anchor can be tailored to the tissue healing, and wherein the metabolites released during degradation do not cause inflammatory responses and are not highly acidic. Furthermore, it would be desirable to identify new anchor designs with higher pullout strengths, or that allow smaller bone holes to be used.

It is an object of the present invention to provide compositions and materials that can be used to improve the osteointegration of soft suture anchors.

It is another object of the invention to provide methods for manufacturing soft suture anchors that can be used to improve the osteointegration of soft suture anchors.

It is a further object of the invention to provide soft suture anchors manufactured from compositions and materials that can be used to improve the osteointegration of soft suture anchors.

It is still another object of the invention to provide methods for manufacturing the anchor component of a soft suture anchor from bioceramics, resorbable materials, and combinations thereof.

It is yet another object of the invention to provide soft suture anchors wherein the anchors have been manufactured from bioceramics, resorbable materials, and combinations thereof.

It is still further an object of the invention to provide soft suture anchors wherein the anchors have been manufactured from resorbable ceramics and resorbable polymers.

It is yet still another object of the invention to provide soft suture anchors with new anchors designs that provide higher pullout strengths and that can be used with smaller bone holes.

SUMMARY OF THE INVENTION

Compositions and materials for making soft suture anchors including materials that improve osteointegration have been developed. These compositions and materials include bioceramics, resorbable materials, and combinations thereof. A preferred embodiment is a soft suture anchor including a resorbable ceramic and a resorbable suture, preferably made of a biodegradable polymer with the properties of poly 4-hydroxybutyrate, P4HB.

The bioceramics, resorbable materials, or combinations thereof are particularly useful when incorporated with currently existing soft suture anchors, such as Biomet JUG-GERKNOT™, Stryker ICONIX™, Smith & Nephew Suturefix Ultra, and ConMed LINVATEC™ Y-knot devices. In this way, the presently disclosed embodiments could improve osteointegration, increase pullout strength, and increase resorption of these currently existing soft suture anchors. Additionally, the application of the presently disclosed bioceramics, resorbable materials, or combinations thereof could result in a decrease in inflammation when compared to currently existing soft suture implants.

DETAILED DESCRIPTION OF THE INVENTION

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes. "Resorbable" as generally used herein means the material is broken down in the body and eventually eliminated from the body.

"Resorbable bioceramic" means a bioceramic that is used to replace or repair damaged tissue in the body, and is eventually resorbed such that the host replaces the implant. Examples include tricalcium phosphate (TCP), biphasic calcium phosphate (BCP), hydroxylapatite, calcium sulfate, calcium carbonate, and other calcium phosphate salt-based bioceramics, including bioactive glasses composed of $SiO_2$, $Na_2O$, CaO and $P_2O_5$ in specific proportions.

"Bioactive agent" is used herein to refer to therapeutic, prophylactic or diagnostic agents, preferably agents that promote healing and the regeneration of host tissue, and also therapeutic agents that prevent, inhibit or eliminate infection agent" includes a single such agent and is also intended to include a plurality.

"Bicomponent" as generally used herein means a structure containing two or more materials.

"Bioceramic" means a ceramic suitable for use or replacement in the human body.

"Ceramic" means an inorganic, nonmetallic solid prepared by the action of heat and subsequent cooling.

"Blend" as generally used herein means a physical combination of different polymers, as opposed to a copolymer formed of two or more different monomers.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, Mass.).

"Copolymers of poly-4-hydroxybutyrate" as generally used herein means any polymer containing 4-hydroxybutyrate with one or more different hydroxy acid units.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Pullout strength" as used herein is measured by inserting a suture anchor into a foam block (20 pcf cellular rigid polyurethane foam with a 3 mm 50 pcf solid rigid "cortical layer", Sawbones), which serves as a bone analogue. A tensile load is applied along the axis of the anchor at a rate of 12.5 mm/s, and the load at failure (N) is recorded.

"Soft suture anchor" means a soft fixation device including an anchor component and a suture component capable of providing a location for attachment of suture in or against a substrate (such as bone), wherein the anchor component is constructed substantially of filamentary material or other soft material such as foam or a material including a PHA polymer, particularly P4HB or copolymer thereof.

II. Implant Components and Materials

Soft suture anchors have been developed wherein at least the anchors include bioceramic material. The bioceramic improves the osteointegration of the anchor into the bone, while maintaining adequate pullout strength to allow fixation of soft tissues to the bone anchor site. In a preferred embodiment, the anchors include a bioceramic that is resorbed and replaced by bone. In a particularly preferred embodiment, the anchors of the soft suture anchors include a bioceramic and a resorbable material. In further embodiments, at least the anchors include resorbable materials or a combination of bioceramics and resorbable materials.

A. Bioceramics

Bioceramics that can be used to prepare the soft suture anchors must be biocompatible and improve the osteointegration of the anchor into the bone. In a preferred embodiment, the bioceramic is a resorbable bioceramic that can be replaced by the body or allows the repair of damaged tissues in the body. Examples of resorbable bioceramics that can be used to prepare the soft suture anchors include tricalcium phosphate ($\alpha$ and $\beta$ forms of tricalcium phosphate (TCP)—with a nominal composition of $Ca_3(PO_4)_2$), biphasic calcium phosphate (BCP), hydroxyapatite (also known as hydroxylapatite), calcium sulfate, calcium carbonate, and other calcium phosphate salt-based bioceramics. Bio-active glasses may also be used. Bioactive glasses include resorbable glasses, and include bioactive glasses composed of $SiO_2$, $Na_2O$, $CaO$ and $P_2O_5$ in specific proportions. The choice of bioceramic and particle size of the bioceramic will depend in part on the desired rate of resorption for the implant, and the design of the implant. In a preferred embodiment, the suture anchor includes $\beta$-TCP, $\alpha$-TCP or a combination thereof. The bioceramics are preferably particulate in nature. The particles may have a size or distribution ranging from nanoparticles to microparticles. In a preferred embodiment, the ceramics have particle sizes of less than 100 microns.

B. Polymers for Preparing Anchors

The anchor components of the soft suture anchors may be prepared from permanent materials, resorbable materials, or combinations thereof. The anchor and the suture of the soft suture anchor may be prepared from the same material or different materials. Examples of resorbable polymers that may be used to prepare the soft suture anchors include, but are not limited to, synthetically or biologically prepared polyesters; polymers including glycolic acid, lactic acid, 1,4-dioxanone, trimethylene carbonate, 3-hydroxybutyric acid, $\epsilon$-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide), or polycaprolactone or combinations thereof. Blends of polymers may also be used to prepare the implants. Preferably the polymer or copolymer will be substantially resorbed within a 3 to 18 month timeframe, and retain some residual strength for at least one to two months, more preferably at least three months.

In a particularly preferred embodiment, poly-4-hydroxybutyrate (P4HB) or a copolymer thereof is used to make the anchor. Copolymers include P4HB with another hydroxyacid, such as 3-hydroxybutyrate, and P4HB with glycolic acid or lactic acid monomer. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for prolonged strength retention. In another preferred embodiment, P4HB may be blended with other absorbable polymers such as homopolymers or copolymers of glycolic acid, lactic acid, p-dioxanone, trimethylene carbonate, $\epsilon$-caprolactone or copolymers containing 4-hydroxybutyrate (4HB), and used to make the anchor.

Examples of permanent polymers that may be used to prepare the anchor component of the soft suture anchor include, but are not limited to, polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(etherurethanes), poly(methylmethacrylate), polyether ether ketone, polyolefins, and poly(ethylene oxide).

C. Sutures for Soft Suture Anchors

The sutures of the soft suture anchors may be monofilaments or multifilaments, or combinations thereof, including sutures including a monofilament and/or multifilament core with a sheath made from an external braid. The sutures may be made from permanent materials or resorbable materials, or hybrid structures of permanent and resorbable materials. The sutures may be substantially solid or hollow, substantially round or substantially flat (having, for example, a tape shape). The suture ends may or may not be needled. Regions of the suture may have a different stiffness from the rest of the thread, for example, to aid suture threading and manipulation. When the soft suture anchor includes more than one suture thread, the suture threads may be made from the same or different materials.

In one embodiment, the sutures are formed of: polyester (including DACRON™ suture), ultrahigh molecular weight polyethylene (including FORCE FIBER™, MAXBRAID™, and ORTHOCORD™, ULTRABRAID™, POWER FIBER™, CP-FIBER, and FIBERWIRE™ sutures, and other sutures derived from DYNEEMA™ fiber).

In a preferred embodiment, the sutures are resorbable and include one or more of the following materials: polymers including glycolic acid, lactic acid, 1,4-dioxanone, trimethylene carbonate, 3-hydroxybutyric acid, 4-hydroxybutyric acid, $\epsilon$-caprolactone, including polyglycolic acid, polylactic acid, polydioxanone, polycaprolactone, poly-4-hydroxybutyrate homopolymer, copolymers of glycolic and lactic acids, such as VICRYL® polymer, MAXON® and MONOCRYL® polymers. In a particularly preferred embodiment, the sutures are Phantom Fiber BIOFIBER sutures (sold by Tornier, Inc., Minneapolis, Minn.) made from a monofilament core of P4HB and an outer braided sheath also made from P4HB.

The sutures may be completely dyed, dyed with a specific pattern, or dyed such that one end of the suture is a different color or pattern than the other end, so that the surgeon can distinguish different threads.

In another embodiment, the anchor, the suture, or both components may be coated to permit or improve the movement of the suture within the anchor component. Suitable coatings include, but are not limited to, polymers or oligomers of ethylene oxide, polymers or oligomers of propylene oxide, or combinations thereof, and polyethylene glycol sorbitan monolaurate.

D. Other Coatings and Modifying Agents

The soft suture anchors may be coated, derivatized, or modified with other agents in order to improve wettability, water contact angle, cell attachment, tissue in-growth, and tissue maturation.

In one embodiment, the soft suture anchors may include cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of these proteins, including fragments or sequences containing the binding domains, having the same binding properties.

In another embodiment, the soft suture anchors may incorporate wetting agents designed to improve the wettability of the surfaces of the implant structures to allow fluids to be easily adsorbed onto the implant surfaces (particularly the anchor), and to promote cell attachment and or modify the water contact angle of the implant surface. Examples of wetting agents include polymers of ethylene oxide and propylene oxide, such as polyethylene oxide, polypropylene oxide, or copolymers of these, such as pluronics. Other suitable wetting agents include surfactants or emulsifiers.

E. Therapeutic, Prophylactic or Diagnostic Agents

The implants may contain bioactive agents. In a preferred embodiment, the agents improve cell attachment, tissue in-growth, and tissue maturation. The implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1B), interleukin-8 (IL-8), and nerve growth factor (NGF), and combinations thereof.

Other bioactive agents include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents.

The bioactive may be proteins such as collagen and antibodies, peptides, polysaccharides such as chitosan, alginate, polysaccharides such as hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

Diagnostic agents include contrast agents, radiopaque markers, or radioactive substances which may be incorporated into the implants.

The implants may also contain allograft material and xenograft materials.

In yet another preferred embodiment, the implants may incorporate systems for the controlled release of the therapeutic or prophylactic agents.

III. Methods of Manufacturing Soft Suture Anchors

A. Soft Suture Anchors Made from Blends of Bioceramics and Polymers

Soft suture anchors have been developed that are made from blends of bioceramic and polymers as opposed to coating bioceramics on polymers. The blends allow much higher levels of incorporation of bioceramic into the anchor, and importantly allow the bioceramic to be dispersed throughout the anchor of the soft suture anchor to promote osteointegration.

(1) Compounding of Polymers and Ceramics

In an embodiment, the blends of bioceramic and polymers are compounded to thoroughly mix the components using a single or twin-screw extruder. Alternatively, the polymer may be dissolved in a solvent, the bioceramic dispersed in the solvent, and the solvent removed by evaporation. Or, the bioceramic and polymer are pre-mixed, or fed directly to an extruder. In a preferred embodiment, the bioceramic is tricalcium phosphate ($\alpha$ and $\beta$ forms of tricalcium phosphate (TCP)—with a nominal composition of $Ca_3(PO_4)_2$), biphasic calcium phosphate (BCP), hydroxylapatite, calcium sulfate, calcium carbonate or other calcium phosphate salt-based bioceramic, or a bioactive glass composed of $SiO_2$, $Na_2O$, $CaO$ and $P_2O_5$ in specific proportions. In a particularly preferred embodiment, the polymer is resorbable. In an even more preferred embodiment, the resorbable polymer is P4HB or copolymer thereof.

The ratio of polymer to bioceramic may be varied according to the desired applications. The formulation of polymer and bioceramic may include up to 70% by volume of the bioceramic, however, more preferably compounded compositions include up to 50% by volume of the bioceramic. In a preferred embodiment, the polymer is compounded with the bioceramic by metering in the desired ratio into a single or twin-screw extruder wherein they are mixed prior to being extruded into pellets.

(2) Preparation of Fibers from Polymer/Bioceramic Blends

In one embodiment, the anchor of the soft suture anchor is made from fibers that are formed from polymer/bioceramic blends. In a preferred embodiment, the polymers filled with bioceramic may be extruded or solution spun to form the fibers. In a particularly preferred embodiment, the fibers are extruded from compounded pellets of polymer/bioceramic. The fibers may be monofilament or multifilament, oriented or unoriented, relaxed or unrelaxed.

In one embodiment the multifilament fibers are prepared with a denier per filament (dpf) of less than 6, more preferably less than 4, and even more preferably less than 3. In another embodiment, the multifilament fibers are prepared with a tenacity of greater than 2 gram/denier, and more preferably greater than 4 gram/denier In a further embodiment, the monofilament fibers are prepared with diameters ranging from 25 microns to 5 mm. In a preferred embodiment, the monofilament fibers have a tensile strength greater than 10 MPa.

In another preferred embodiment, the monofilament and multifilament fibers are extruded from blends of bioceramic and resorbable polymer. In a particularly preferred embodiment, the monofilament and multifilament fibers are extruded from blends of bioceramic and P4HB.

(3) Preparation of Anchors from Polymer/Bioceramic Fibers and Assembly of Soft Suture Anchors The monofilament or multifilament fibers, or combinations thereof, made from blends of polymer and bioceramic, may be converted by textile processing methods into anchors suitable for use in soft suture anchors. In one embodiment, tubes, sheaths, or sleeves are manufactured by braiding, weaving or knitting of the fibers. In some embodiments, the tubes, sheaths, and sleeves are formed so that they will allow the suture of the soft suture anchor to slide inside the anchor component. This is particularly important in rotator cuff surgery where the surgeon needs to manipulate the suture to correctly reattach the cuff.

The soft suture anchors may contain more than one suture as well as sutures of different sizes and structures (e.g. monofilament sutures, braided sutures, permanent sutures, hybrid sutures, and resorbable sutures). The anchor component can be prepared with a range of different sizes to accommodate different types and quantities of sutures, and allow free movement of the suture or sutures within the anchor component. In a preferred embodiment, the anchors have diameters ranging from 0.3 mm to at least 5.0 mm. In an embodiment, the anchor tube, sheath or sleeve has at least one opening positioned along the length (i.e. the wall) of the anchor, extending from the interior to the exterior surface of the anchor or utilizes the open ends of a tubular sleeve or sheath. In a more preferred embodiment, there are four or more openings positioned along the length of the anchor. The openings may be formed during the textile processing process, or formed subsequently using a laser or mechanical tool such as a knife, punch or needle. The openings on the anchor are of a sufficient size to allow at least one suture of the suture anchor to pass through the openings. In an embodiment, the soft suture anchor is formed by threading the suture into one end of the tube, sheath or sleeve anchor, passing the suture from the interior through the first opening to the exterior of the anchor, and then threading the suture back through the second opening in the tube, sheath or sleeve to the interior of the anchor. The suture thread may be passed in a similar manner through any additional openings on the surface of the anchor, before it exits through the opening at the other end of the tube, sheath or sleeve. The suture thread may be radially wound into the tubular structural wall with one or two of the suture threads protruding out of the tube surface for anchoring to tissues. Additional sutures may also be radially wound or threaded through the openings, or alternatively, just passed through the anchors without passing through any openings on the surfaces of the tubes, sheaths or sleeves. The tubes, sheaths, and sleeves are formed so that they are pliable, compressible, and expandable, and can form a U-shape upon initial insertion into the bone hole, and change shape within the bone hole when tension is applied to one or more ends of the suture threads exiting the tubes, sheaths, and sleeves. The tubes may also be layered together where one or more tubular anchors can fit inside another tubular anchor to increase anchoring bulk. The openings in the tubes, sheaths, and sleeves are placed so that the anchor compresses the bone within the bone hole when tension is applied to one or both ends of the suture(s). In a particularly preferred embodiment, the anchor includes a combination of monofilament and multifilament fibers wherein at least the monofilament or multifilament fibers are formed from a blend of P4HB and a bioceramic. In an even more preferred embodiment, multifilament fibers formed from a blend of P4HB and bioceramic are braided to make the anchor tubes, sheaths and sleeves.

In an alternate embodiment, the anchor includes a fibrous construct such as a tape, ribbon or cylinder that is made from the fibers of polymer and bioceramic. The suture of the suture anchor passes from one side of the tape, ribbon or cylinder to the other side in at least three places. Increasing the number of times the suture passes from one side of the fibrous construct to the other increases the number of pleats that form in the fibrous construct when tension is applied, causing the thickness of the deployed anchor to increase. In a preferred embodiment, the suture passes through the fibrous construct either substantially parallel to the longitudinal axis of the construct, or in a staggered manner. In another embodiment, the fibrous construct may include more than one suture, and as described above, the suture or sutures may be dyed, patterned, coated, and stiffened. In a further embodiment, the sutures may incorporate slipknots near the ends of the fibrous constructs so that the fibrous anchor transitions from an un-deployed state to a deployed state when tension is applied to the sutures. The dimensions of the fibrous construct will depend on the specific application. In an embodiment, the fibrous construct will have a length of 5 to 200 mm, and more preferably 20 to 80 mm, and a width of 0.3-5 mm or more. The fibrous construct is formed so that it is pliable, compressible, and can be formed into a U-shape, Y-shape, or other suitable shape upon initial insertion into the bone hole, and change shape within the bone hole when tension is applied to one or more ends of the suture threads. In a preferred embodiment, the fibrous anchor construct is a tape, ribbon or cylinder that is made from monofilament or multifilament fibers, or combinations thereof, derived from blends of bioceramic and a resorbable polymer, and more preferably a bioceramic and P4HB. The tape, ribbon or cylinder may be formed by braiding, knitting, weaving, or using a non-woven processing technique such as melt-blowing, dry spinning, or electrospinning.

In yet another embodiment, the anchor includes a braided, knitted or woven tube, sheath or sleeve made from fibers of the bioceramic and polymer described above, wherein the anchor has two openings positioned between the first and second ends of the anchor such that one end of a suture can be passed inside the first opening of the anchor, along a passageway inside the anchor, and out of the second opening in the flexible anchor. In a preferred embodiment the openings are placed about one-quarter and three-quarter lengths from either end of the anchor. The anchor is flexible enough to allow the ends of the suture to be held approximately parallel such that the anchor forms a U-shape for insertion into the bone hole. The material between the ends of the anchor and the first and second openings provides additional resistance when the anchor is inserted into a bone hole, and tension is applied to the suture ends to raise the mid-section of the anchor and cause bunching and compression of the cancellous bone to secure the anchor. In a particularly preferred embodiment, the flexible anchor is made from monofilament or multifilament fibers, or combinations thereof, derived from blends of bioceramic and a resorbable polymer, more preferably a bioceramic and P4HB that have been braided, knitted, or woven into a tube, sheath or sleeve. The openings may be formed during textile processing or alternatively formed by punching or cutting holes.

In a further embodiment, the anchor of the soft tissue anchor may be a foam, film or similar compliant, flexible, foldable, squashable, squeezable, deformable, limp, flaccid, elastic, low-modulus, soft, perforated material that permits the anchor to change shape after implantation in the bone hole. Suture is passed through the foam (or similar compliant material) so that it enters the anchor between the first and second ends of the anchor, is threaded inside the foam or sponge, and out of a second opening near the other end of the anchor. In a preferred embodiment the suture enters and exits the foam at a distance of one-quarter and three-quarter lengths from either end of the anchor. The foam is flexible enough to allow the ends of the suture to be held approximately parallel such that the anchor forms a U-shape for insertion into the bone hole. The material between the ends of the anchor and the first and second openings provides additional resistance when the anchor is inserted into a bone hole, and tension is applied to the suture ends to raise the mid-section of the anchor and cause bunching and compression of the cancellous bone to secure the anchor. In a particularly preferred embodiment, the soft tissue anchor includes foam made from a blend of a bioceramic and a resorbable polymer, preferably P4HB.

In still another embodiment, the anchor includes a slotted tube, cylinder, sheath or sleeve, made from fibers of the polymers and bioceramics, wherein the slotted anchor has at least two slots between the inner and outer surfaces of the tube, cylinder, sheath or sleeve that run parallel to the longitudinal axis of the anchor, and more preferably at least four slots. The length of the slots may be varied, however, the slots must be less than the length of the anchor, and not protrude into either end of the anchor. The formation of slots in the longitudinal axis results in the formation of longitudinal struts on the outside of the anchor. Suture is threaded into the slotted tube, through the longitudinal axis of the anchor, and the suture tied at one end or passed through a solid cone or pledget. (For clarification, the suture passes directly through the center of the anchor, and does not pass through any of the slots). The diameter of the knot is sized to prevent the knotted end of the suture from passing inside the slotted tube when tension is applied from the other end of the suture, and the knot is formed. The diameter of the knot should also preferably be no larger than the diameter of the slotted anchor. Additional strands of suture may be threaded through the longitudinal axis of the anchor, and either knotted in a similar manner to the first suture thread, or secured to another thread, such that additional suture ends which can be used for fixation protrude from the same end of the slotted anchor. The threaded slotted anchor is inserted into a bone hole with the knot entering the bone hole first, followed by the slotted anchor component, with the unknotted ends of the suture threads exiting the bone hole. The anchor is fixed in position by holding the slotted tube in place, for example, with an inserter, and applying tension to the suture(s). Applying tension to the suture causes the knot to compress the slotted anchor, forcing the struts into the cancellous bone. In a preferred embodiment, monofilament or multifilament fibers, or combinations thereof, derived from blends of P4HB and bioceramic are braided, weaved or knitted to form the slotted anchor. In another embodiment, the slotted tube may be formed by melt-extrusion, and slots cut in the extruded tube by laser or mechanical means. In a particularly preferred embodiment, the melt-extruded slotted tubes are made from blends of a bioceramic and a resorbable polymer, preferably P4HB.

In yet a further embodiment, the anchor includes a slipknot made from monofilament or multifilament suture, or combinations thereof. The slipknot is formed at one end of the suture of the soft suture anchor, and the other end is used, for example, for the fixation of soft tissue. In a particularly preferred embodiment, the slipknot is a hangman's noose. The slipknot has an initial diameter suitable for placement within a bone hole, and can compress cancellous tissue within a bone hole upon tightening. If desired, additional suture threads may be used to form the soft tissue anchor. These threads may be attached to the first thread, preferably by incorporation of two or more threads into the slipknot. The slipknot and any other section of the suture that is implanted within the bone hole is preferably made from monofilament or multifilament fiber, or combinations thereof, that are prepared from blends of a bioceramic and a resorbable polymer, preferably P4HB.

The soft suture anchors have a minimum of pullout strength of 25 N (fixation strength). In a preferred embodiment, the soft suture anchors have pullout strengths of at least 50 N, and more preferably a pullout strength of at least 100 N.

(4) Coating of Soft Suture Anchors

If desired, the implants may include bioactive agents, contrast agents, radiopaque markers or radioactive substances. These agents may be added at any stage during the manufacture of the soft suture anchors including during the formulation process, during the processing of the components, or by coating the finished devices.

The soft suture anchors may also be coated with bioceramics to further increase osteointegration. In one embodiment, fibers used to prepare the anchors or the finished anchors may be coated with emulsions of bioceramics. In a particularly preferred embodiment, P4HB fibers made from blends of P4HB and bioceramic may be coated with emulsions of bioceramics prior to making the anchors, or the anchors may be coated once they have been fabricated. The amount of bioceramic coated on the fibers or anchors may be varied according to the application. In cases where the suture anchors are used to fix bone to bone, the suture of the soft suture anchor may also be coated with bioceramics.

Although it is preferred that the soft suture anchors are made from blends of resorbable polymer with resorbable bioceramics, it is also the intent to provide soft suture anchors made from P4HB and from P4HB coated with bioceramic. The methods described herein may be used to form anchors for soft suture anchors from P4HB and P4HB fibers. Soft suture anchors can also be made wherein the anchor is made from P4HB fibers and the suture of the suture anchor is made from P4HB. In a preferred embodiment, the soft suture anchor includes the Phantom Fiber BIOFIBER® suture. In a particularly preferred embodiment, the soft suture anchor including the Phantom Fiber BIOFIBER® suture and a P4HB anchor further includes a coating of bioceramic.

IV. Use and Deployment of the Soft Suture Anchors

Following assembly and prior to insertion, the soft suture anchors are sterilized. The specific sterilization method will depend among other considerations on the materials used to prepare the soft suture anchors, and can be selected from the list including gamma-sterilization, e-beam irradiation, ethylene oxide, and steam sterilization. In a preferred embodiment, soft suture anchors including P4HB are sterilized using cold ethylene oxide gas.

In one embodiment, the soft suture anchors may be used to secure tissue to bone by, for example, drilling a bone hole, forming the anchor into a U-shape, Y-shape, fish-like shape, or similar shape suitable for inserting in a bone hole, inserting the shaped anchor into the bone hole so that the suture threads protrude from the bone hole, and pulling on the suture threads to compress the bone anchor within the bone hole. At least one of the suture threads protruding from the bone hole is passed through tissue, using, for example, a needle or pre-attached needle, and the tissue is secured to the bone by securing the suture. In another embodiment, the soft suture anchors are used by inserting a slotted tube or slipknot into a bone hole, and applying tension to the slotted tube or slipknot to cause compression on the cancellous bone in the bone hole.

In an embodiment, the bone hole is made using a drill and drill guide, and the drill or drill guide may be marked to ensure the proper drilling depth is made. Alternatively, there may be a hard stop between the drill and drill guide for this purpose. The depth of the drill hole will depend on the application, but in general will be about 10-30 mm, and must pass through the cortical bone into the cancellous bone. Although the bone holes will be of different sizes to accommodate different suture sizes and numbers of sutures, the diameter of the bone hole is chosen such that the anchor of the soft suture anchor is a close-fit, for example, when a U-shaped, fish-like shape, or Y-shaped anchor is folded or compressed on itself and inserted in the bone hole, or when a slotted tube is inserted.

In a preferred embodiment, the soft suture anchor is inserted into the bone hole using an inserter, and may optionally be firmly seated by striking the inserter with a mallet one or more times. The surgeon may place the soft suture anchor on the inserter prior to use, or the soft suture anchor may be pre-loaded on the inserter, and optionally sold as a kit. If desired, the inserter may have a marking to assist in the correct placement of the soft suture anchor, for example, at the correct depth. The anchor is placed on the distal end of the inserter. The distal end may be a blunt end, forked end, or active clamping structure.

After deployment of the anchor, a suture thread protruding from the anchor site may be pushed or pulled through soft tissue (using, for example, a needle or needle that has been pre-attached to the suture fiber), and used to pull the soft tissue to the reattachment site, or adjacent to the bone hole. Additional suture threads may be used to tie the soft tissue, and create additional points of fixation.

The soft tissue may be rotator cuff, shoulder labrum, hip labrum, forehead skin (in the case of a facelift) or any other soft tissue that can be reattached to bone at the site of a bone hole. The soft suture anchors may also be used to secure soft tissue to soft tissue, such as in meniscal repair, as well as to secure bone to bone, for example, in fracture fixation.

Those skilled in the art will understand that features, elements and functions described in this description may be mixed, and those combinations are expressly contemplated herein.

Methods of manufacturing are demonstrated by reference to the following non-limiting examples.

Example 1: Compounding of P4HB and β-TCP

P4HB (Mw 350 kDa) was compounded with β-TCP (mean particle size of 20±5 microns) using a Leistritz twin-screw extruder at 13-TCP loadings on a weight basis (wt-%) of up to 58%. The barrel temperature of the extruder increased from 30° C. at the feed zone to 160° C. at the die. The screws were rotated at 135 rpm, and extruded strands were cooled in a water bath before being pelletized.

Example 2: Compounding of P4HB with Calcium Carbonate

A twin-screw microcompounder (DSM Xplore™ 15 cm$^3$) was used to compound P4HB with calcium carbonate (44 wt %) at a temperature of 220° C. The calcium carbonate had a nominal particle size of 10 microns.

Example 3: Extrusion of Multifilament Fibers of P4HB/β-TCP

Blended pellets of P4HB/β-TCP prepared according to Example 1 may be dried using a rotary vane vacuum pump system to a moisture content of less than 300 ppm. The dried resin may be transferred to a feed hopper with a nitrogen purge to keep the pellets dry, gravity fed into a chilled feeder section, and introduced into an extruder barrel, for example, 0.75 inches in diameter and 25.69 inches long via an extrusion screw with 30:1 L/D ratio. A preferred extruder barrel contains four heating or extrusion zones. The heated and softened resin from the extruder may be fed into a heated metering pump (melt pump), and from the melt pump the extruded resin fed into the heated block. The spin head houses a spin pack including filtering media (screens) and spinnerets containing the desired number of holes for forming the individual filaments of the yarn, for example, 15, 30 and 60 or more holes. The extruded filaments exit the spinneret, pass through a hot chimney, and are preferably air-cooled until they solidify inside a contained, clear tube. The resulting yarn may be passed through a spin finish applicator, over two rotating godets, and collected on a precision winder as the yarn exits the second godet. Preferred spin finishes include polymers or oligomers of ethylene oxide, polymers or oligomers of propylene oxide, combinations thereof, and polyethylene glycol sorbitan monolaurate. The denier of the yarn can range significantly depending on the number of holes and speed of the godets. A preferred range is 10-440 denier.

In a preferred method, orientation of the P4HB/β-TCP yarn is accomplished offline, although it can also be done inline. In a preferred method, the extrudate may be collected onto spools and then three sets of paired godets can be used to orient the yarn from a payoff system holding the extrudate collection spool. The extruded yarn may be rewet via a controlled pump speed spin finish applicator. In a preferred method, the yarn is hot stretched.

Example 4: Extrusion of Monofilament Fibers of P4HB/β-TCP

Blended pellets of P4HB/β-TCP prepared according to Example 1 may be dried using a rotary vane vacuum pump system to a moisture content of less than 300 ppm. The dried resin may be transferred to a feed hopper with a nitrogen purge to keep the pellets dry, gravity fed into a chilled feeder section, and introduced into an extruder barrel (1.5 inch diameter) fitted with an extrusion screw (with a 30:1 L/D ratio). The extruder barrel preferably contains 5 heating zones (or extrusion zones). The heated and softened resin from the extruder may be fed into a heated metering pump (melt pump) and from the melt pump the extruded resin fed into the heated block and spinneret assembly. Processing profile ranges from: 40° C. to 260° C. for temperatures, and 2.75 MPa to 14 MPa for pressures. The molten filaments may be water quenched and conveyed into a three-stage orientation, (optionally with inline relaxation), before winding of the P4HB/β-TCP monofilaments on spools.

Example 5: Preparation of a Braided Soft Suture Anchor of P4HB/β-TCP

Monofilament fibers according to Example 4 may be braided, knitted, or weaved to form a P4HB/β-TCP soft suture anchor. The soft suture anchor is then coupled to a suture such that the suture passes through the anchor along an internal channel inside the P4HB/β-TCP soft suture anchor. During use, the ends of the suture can be manipulated so that the P4HB/β-TCP soft suture anchor forms substantially a U-shape for insertion into a drill hole made in bone. When inserted into the drill hole, the ends of the P4HB/β-TCP soft suture anchor provide additional resistance when tension is subsequently placed on the suture. This tension causes a middle portion of the P4HB/β-TCP soft suture anchor to rise, bunch, and compress into the cancellous bone, securing the P4HB/β-TCP soft suture anchor in the drill hole. Insofar as the anchor is made from P4HB/13-TCP monofilaments (See Example 4), the pull-out force is increased and thus the drill hole size may be less than what is required with currently available soft suture anchors consisting of polyester with a similar design, such as the Biomet JUGGERKNOT™. Moreover, the P4HB/β-TCP soft suture anchor reduces inflammation and increases osteointegration as compared to currently available soft suture anchors consisting of polyester with a similar design.

The P4HB/β-TCP soft suture anchor may be used in conjunction with a suitable inserter device to allow for a completely suture based implant. In some situations the surgeon will load the P4HB/β-TCP soft suture anchor onto the inserter device immediately before use. In other situations, the P4HB/β-TCP soft suture anchor is pre-loaded onto the inserter device and sold as kit. The P4HB/β-TCP soft suture anchor and inserter device are sterilized by appropriate methods, such as gassing with cold ethylene oxide, prior to use.

Example 6: Preparation of a P4HB/O-TCP Tape for Use as a Soft Suture Anchor

The P4HB/β-TCP monofilament fibers from Example 4 may be braided, weaved, knitted, bonded, or laminated, forming a P4HB/β-TCP flat tape. A suture is then passed through the P4HB/β-TCP flat tape in at least three passing locations along the length of the P4HB/β-TCP flat tape forming a P4HB/β-TCP flat tape suture. The suture may be made out of P4HB/β-TCP monofilaments. The first passing location is nearest to the first end of the P4HB/β-TCP flat tape, the last passing location is nearest to the second end of the P4HB/β-TCP flat tape, and there is at least one intermediate location between the first passing location and the last passing location. The suture may freely slide within the P4HB/β-TCP flat tape, or it may be fixed to the P4HB/β-TCP flat tape.

When deployed into a drill hole in a bone, tension is applied to the ends of the suture that passes through the P4HB/β-TCP flat tape. The applied tension changes the shape of P4HB/β-TCP flat tape suture, causing it to become more compact and expand outwardly. The outward expansion anchors the P4HB/β-TCP flat tape suture in the drill hole. Stated differently, the applied tension causes the P4HB/β-TCP flat tape suture to fold in an accordion fashion, thus increasing the overall diameter of the P4HB/β-TCP flat tape suture and securing it in the drill hole.

Insofar as the P4HB/β-TCP flat tape suture is made from P4HB/β TCP monofilaments, the pull-out force is increased and thus the drill hole size may be less than what may be required for flat tape sutures that do not incorporate resorbable materials or bioceramics. Further, the use of P4HB/β-TCP monofilaments, in at least the flat tape, may reduce deleterious inflammation and increase osteointegration as compared to flat tape sutures that do not incorporate resorbable materials or bioceramics.

Example 7: Preparation of a Braided Soft Suture Anchor of P4HB/β-TCP with No Ears The braided monofilament fibers from Example 5 may also be used make an anchor without the excess material between the end of the braided anchor and the first and last hole. This anchor relies on the amount of pleats added to the braided anchor to increase its diameter when deployed in cancellous bone.

Example 8: Preparation of a Multilayer Braided Soft Suture Anchor of P4HB/β-TCP The braided monofilament fibers from Example 5 may also be layered together such that one braided anchor can fit inside another braided anchor and so forth, still allowing a suture to pass through the center of the anchor.

Example 9: Preparation of a Slotted Tube Soft Suture Anchor of P4HB/β-TCP

Tubes of P4HB/β-TCP can be extruded, cut or slotted so that they form struts when compressed. A suture may then be passed inside the slotted tube. The suture may have a knot formed at its end with sufficient diameter to prevent the knotted suture thread from passing inside the slotted tube when tension is applied from the other end of the suture.

Figure 1A:
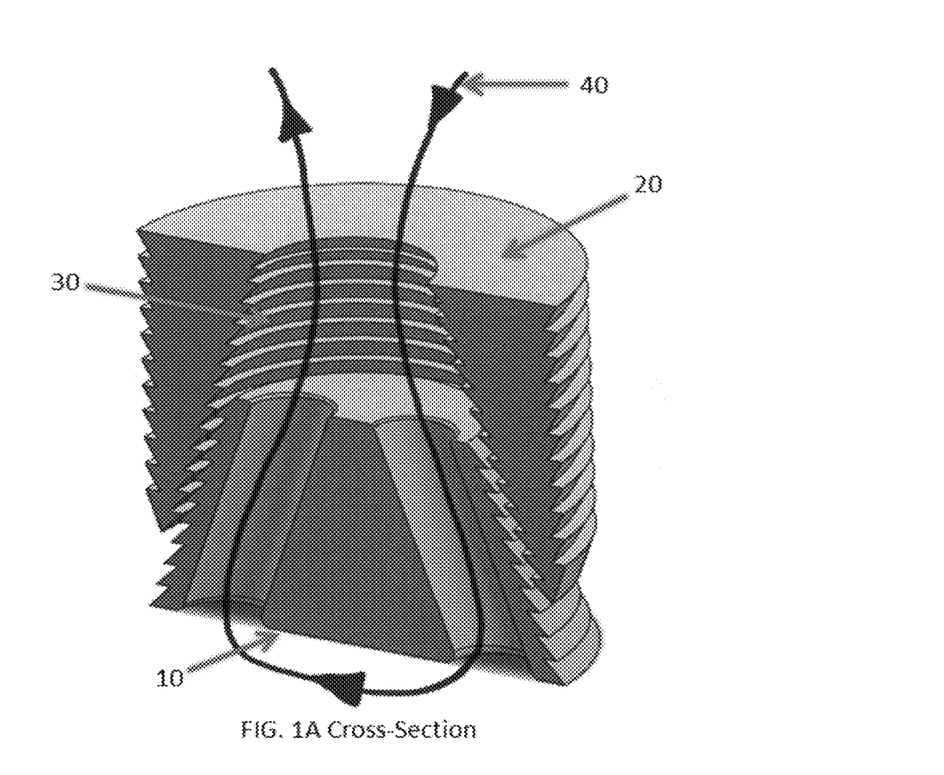
FIGS. 1A and 1B are diagrams of a mating cone (10) and collar anchor (20). The anchor (20) comprises a flexible collar with a taper (30) that mates with a cone (10). The suture (40) is looped through both the collar and cone. Lateral compression occurs in vivo as the cone mates with the collar.
Figure 1B:
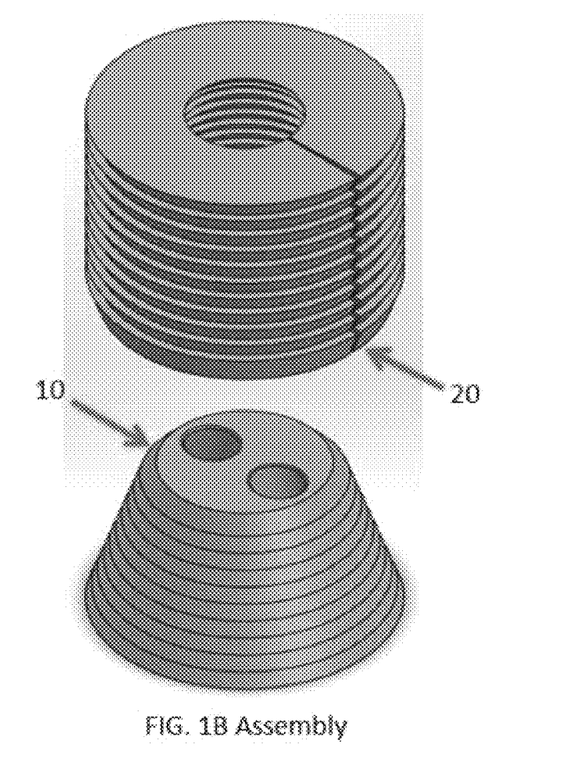

Example 10: Preparation of a Soft Suture Anchor with a Cone and Collar Anchor An anchor is either machined, molded, or 3D printed to form a two piece anchor system (FIG. 1A) the first piece is C shaped flexible cylindrical collar (20) with conical inside surface (30) and a matting cone (10) to fit inside the flexible collar. The cone (10) is fitted with two through holes to allow for passage of sutures. The two piece anchor is loosely assembled as shown in (FIG. 1A). One end of the suture (40) is passed through the top of the collar (20) and guided into one of the holes on top of cone (10). The suture end (40) is then pulled through the first hole and looped into the bottom of the second hole of the cone then guided to exit through the top of the collar (20). During initial insertion into the bone hole the two pieces are loosely mated as shown in (FIG. 1A). After insertion the ends of suture (40) are pulled up, this forces the cone (10) to slide into the flexible collar (20) which will be forced to spring open against the concellous bone and lock in place.

Figure 2A:
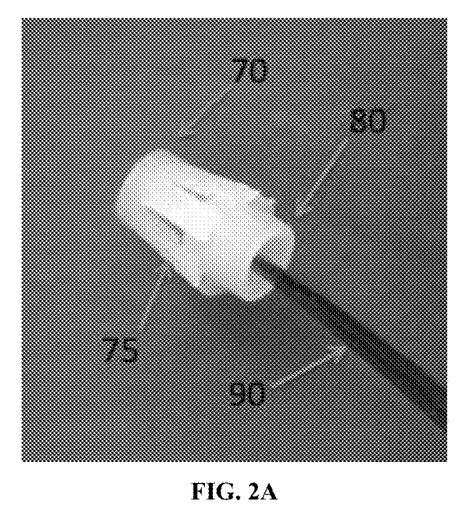
FIGS. 2A and 2B show a two-piece anchor with suture (90) consisting of a base (70) with hanging struts (75) and a ring (80) before and after in vitro deployment. The ring (80) contains a tapered lip leading to a notched edge (85) that snaps into the hanging struts (75) of the base (70). In vivo, the hanging struts compress into the cancellous bone as the ring snaps into the base and pushes the struts out.
Figure 2B:
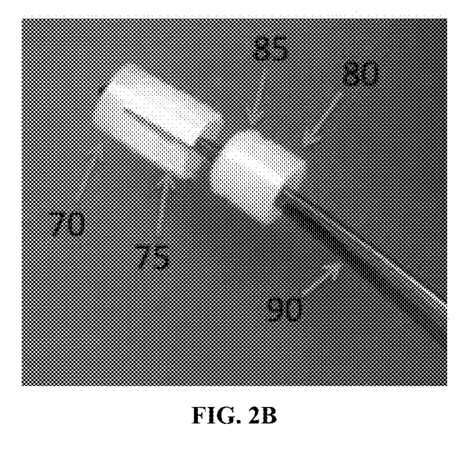

Example 11: Preparation of a Soft Suture Anchor with a Ring and Hinging Struts An anchor is machined, molded, or 3D printed to form a two piece anchor system (FIG. 2) in which the suture (90) is passed through a ring (80) and then through the base (70) of the other half of the anchor with hinging struts (75). The ring has a tapered lip that leads to a notch (85) on the outer surface that goes around the circumference. The base of this system has hinging struts (75) that snap into the notch (85) on the separate ring (80). The suture (90) may be passed through the ring, looped through the base, and back through the ring. When tension is applied to the suture the struts spread open and snap onto the notch of the ring, pushing and locking the anchor into the cancellous bone.

Example 12: Melt Extrusion of P4HB Monofilament, and Preparation of P4HB Monofilament Soft Suture Anchors Bulk P4HB resin in pellet form was dried to under 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and an eight hole spinneret assembly. Processing profile ranges from 40° C. to 260° C. for temperatures, and 400 psi to 2000 psi for pressures, were used. The molten filaments were water quenched and conveyed into a three-stage orientation, with inline relaxation, before winding of the monofilaments on spools. The monofilament fibers may be further processed according to Example 5 by braiding, knitting, or weaving to form a P4HB soft suture anchors.

Example 13: Melt Extrusion of P4HB Multifilament, and Preparation of P4HB Multifilament Soft Suture Anchors P4HB (Tepha, Inc., Lexington, Mass.) (Mw 200-600K) was extruded into P4HB multifilament using the extruder operating conditions set forth in Table 1, and spinnerets with 15, 30 and 60 holes, and as further disclosed in WO 2011/119742 to Martin et al.

TABLE 1

Extruder Operating Conditions for P4HB Multifilament

| Feed | 1 | 2 | 3 | 4 |
|---|---|---|---|---|
| 15° C. ± 10° C. | 75° C. ± 40° C. | 180° C. ± 50° C. | 215° C. ± 40° C. | 250° C. ± 40° C. |

| Pump | Block | Spinneret | Chimney | Extruder RPM |
|---|---|---|---|---|
| 230° C. ± 30° C. | 230° C. ± 30° C. | 230° C. ± 30° C. | 110° C. ± 60° C. | 1 ± 1 |

| Take Up | | | Pressure | | Melt Pump |
|---|---|---|---|---|---|
| G1 MPM | G2 MPM | SF RPM | In | Out | RMP |
| 10 ± 10 | 10 ± 11 | 5 ± 5 | 1400 ± 80 | 600 ± 400 | 16 ± 9 |

The P4HB yarn extrudate was oriented offline using 3 sets of paired godets using the conditions for orientation set forth in Table 2. P4HB Soft suture anchors made from P4HB multifilament fibers may be formed by braiding, knitting or weaving.

TABLE 2

Orientation Conditions for P4HB Multifilament

| Speed (MPM) | | | Roll Temperature (° C.) | | |
|---|---|---|---|---|---|
| GP 1 | GP 2 | GP 3 | GP 1 | GP 2 | GP 3 |
| 10 | 60 ± 20 | 60 ± 20 | Ambient | 56 ± 10 | 40 ± 10 |

Example 14: Preparation of P4HB Slotted Tubes for Use in Soft Suture Anchors Polymer tubes with an inner diameter of 1.0 or 1.4 mm and a wall thickness of 150 µm were fabricated by injection molding, extrusion or dip-coating of P4HB. The polymer tubes were then machined with a $CO_2$ laser for the manufacture of slotted tubes suitable for use as soft suture anchors.

We claim:

1. A soft suture anchor comprising a suture component and an anchor component wherein the anchor component comprises fibers comprising a blend of a bioceramic and one or more resorbable polymers, wherein the bioceramic is dispersed in the fibers of the anchor, and wherein the suture component is permanent, resorbable, a hybrid of permanent and resorbable materials, monofilament, braided, single or multiple threads.

2. The soft suture anchor of claim 1 wherein the bioceramic is resorbable.

3. The soft suture anchor of claim 2 wherein the bioceramic is resorbable and selected from the group consisting of α-tricalcium phosphate (α-TCP), β-TCP, or a combination of α- and β-TCP, biphasic calcium phosphate (BCP), hydroxylapatite, calcium sulfate, calcium carbonate, or a calcium phosphate salt-based bioceramic.

4. The soft suture anchor of claim 1 wherein the the one or more resorbable polymers is selected from the group consisting of poly(orthoester), polyanhydride, poly(phosphazene), polyhydroxyalkanoate, polycarbonate, tyrosine polycarbonate, polyamide, polypeptide, poly(amino acid), polyesteramide, poly(alkylene alkylate), polyether, polyethylene glycol, polyethylene oxide, polyvinyl pyrrolidone, polyurethane, polyetherester, polyacetal, polycyanoacrylate, poly(oxyethylene)/poly(oxypropylene) copolymer, polyacetal, polyketal, polyphosphate, polyphosphoester, polyalkylene oxalate, polyalkylene succinate, poly(maleic acid), silk, recombinant silk, chitin, chitosan, polysaccharide, and polymers comprising glycolic acid, lactic acid, 1,4-dioxanone, trimethylene carbonate, 3-hydroxybutyric acid, 4-hydroxybutyrate, and β-caprolactone, including polyglycolic acid, polylactic acid, polydioxanone, polycaprolactone, copolymers of glycolic and lactic acids, polyacrylic acids, and poly(lactide-co-caprolactone).

5. The soft suture anchor of claim 4 wherein the the one or more resorbable polymers is poly-4-hydroxybutyrate or copolymer thereof.

6. The soft suture anchor of claim 1 wherein the the one or more resorbable polymers in the blend is selected from the group consisting of polymers and copolymers of ethylene and propylene, including ultra-high molecular weight polyethylene, ultra-high molecular weight polypropylene, nylon, polyesters, poly(ethylene terephthalate), poly(tetrafluoroethylene), polyurethanes, poly(ether-urethanes), poly(methylmethacrylate), polyether ether ketone, and poly(ethylene oxide).

7. The soft suture anchor of claim 1 wherein the suture component is undyed, dyed or patterned.

8. The soft suture anchor of claim 1 wherein the suture component is permanent and is made from one or more of the following: ultra-high molecular weight polyethylene, ultra-high molecular weight polypropylene, nylon, polyester, poly(ethylene terephthalate), poly(tetrafluoroethylene), polyurethane, or poly(ether-urethane).

9. The soft suture anchor of claim 1 wherein the suture component is resorbable made from polymers comprising glycolic acid, lactic acid, 1,4-dioxanone, trimethylene carbonate, 3-hydroxybutyric acid, 4-hydroxybutyric acid, ϵ-caprolactone, including polyglycolic acid, polylactic acid, polydioxanone, polycaprolactone, poly-4-hydroxybutyrate homopolymer or copolymers thereof.

10. The soft suture anchor of claim 1 wherein the anchor component is made by braiding, knitting, weaving, tying, injection molding, extrusion, including fiber extrusion, film extrusion, and tube extrusion, 3-D printing, molding or machining.

11. The soft suture anchor of claim 10 wherein the anchor component comprises (i) one or more slivers of film, (ii) a slotted tube, (iii) a ring and hinging struts, (iv) cone and collar, (v) braid or braids of monofilament fiber, multifilament fiber, or combinations thereof, (vi) a flat tape, (vii) a foam, (vi) a tube, sleeve, sheath, ribbon, tape or cylinder, or (vii) a slipknot including a hangman's noose.

12. The soft suture anchor of claim 1 further comprising a therapeutic, prophylactic or diagnostic agent.

13. The soft suture anchor of claim 1 further comprising a contrast agent, radiopaque marker or radioactive substance.

14. The soft suture anchor of claim 1 further comprising a bioceramic coating.

15. The soft suture anchor of claim 1 wherein the soft suture anchor has a pullout strength of at least 25 N.

16. The soft suture anchor of claim 1 wherein the soft suture anchor is configured to be used to fix soft tissue to bone and bone to bone.

17. The soft suture anchor of claim 1 wherein the soft suture anchor is configured to be used in Bankart lesion repair, SLAP lesion repair, acromion-clavicular repair, capsular shift/capsulolabral reconstruction, deltoid repair, rotator cuff tear repair, biceps tenodesis, foot and ankle medial/lateral repair and reconstruction, mid- and forefoot repair, Hallux valgus reconstruction, metatarsal ligament/tendon repair and reconstruction, Achilles tendon repair, ulnar or radial collateral ligament reconstruction, lateral epicondylitis repair, biceps tendon reattachment, knee extra-capsular repair, iliotibial band tenodesis, patellar tendon repair, VMO advancement, knee joint capsule closure, hand and wrist collateral ligament repair, scapholunate ligament reconstruction, tendon transfers in phalanx, volar plate reconstruction, acetabular labral repair, plastic and reconstructive surgery including forehead lifting, brow lifting, eyelid lifting, facelift, neck lift, breast reconstruction, breast reduction, breast augmentation, mastopexy, pelvic floor reconstruction, urethral suspension, anterior ligament repair, spinal repair, or fracture fixation.

18. A method of preparing the soft suture anchor of claim 1 comprising providing powder or pellets of polymer and bioceramic, melting and extruding a blend of the polymer and the bioceramic, extruding fibers from the blend of the polymer and the bioceramic, and forming the anchor component by braiding knitting or weaving the fibers wherein the bioceramic is dispersed in the fibers, the method further comprising combining the anchor component with a suture component, wherein the suture component is permanent resorbable, a hybrid of permanent and resorbable materials, monofilament braided, single or multiple threads.

19. A method for securing soft tissue to bone comprising forming a hole in a bone, inserting the anchor of the soft suture anchor of claim 1 into the hole, retaining the anchor in the hole, changing the shape of the anchor so that it is retained in the hole, and using the suture of the soft suture anchor to secure soft tissue to the reattachment site, or adjacent to the bone hole.

20. The soft suture anchor of claim 1, wherein the fibers of the anchor component do not include ultrahigh molecular weight polyethylene.

* * * * *

UNITED STATES PATENT AND TRADEMARK OFFICE
CERTIFICATE OF CORRECTION

PATENT NO.       : 9,655,609 B2
APPLICATION NO.  : 14/328210
DATED            : May 23, 2017
INVENTOR(S)      : Said Rizk et al.

It is certified that error appears in the above-identified patent and that said Letters Patent is hereby corrected as shown below:

In the Specification

Column 3, Line 5; replace "new anchors" with --new anchor--.
Column 3, Line 18; replace "poly 4-hydroxybutyrate" with --poly-4-hydroxybutyrate--.
Column 8, Line 60; replace "4 gram/denier" with --4 gram/denier.--.
Column 13, Line 57; replace "13-TCP loadings" with --β-TCP loadings--.
Column 15, Line 15; replace "P4HB/13-TCP monofilaments" with --P4HB/β-TCP monofilaments--.
Column 15, Line 29; replace "sold as kit" with --sold as a kit--.
Column 15, Line 34; replace "P4HB/O-TCP Tape" with --P4HB/β-TCP Tape--.
Column 16, Line 8; replace "also be used make an anchor" with --also be used to make an anchor--.
Column 16, Line 52; replace "concellous" with --cancellous--.

In the Claims

Claim 4, Column 18, Line 38; please replace "the the one" with --the one--.
Claim 5, Column 18, Line 56; replace "the the one" with --the one--.
Claim 6, Column 18, Line 59; replace "the the one" with --the one--.
Claim 9, Column 19, Line 10; replace "resorbable made" with --resorbable and made--.
Claim 18, Column 20, Line 24; replace "braiding knitting or" with --braiding, knitting, or--.
Claim 18, Column 20, Line 30; replace "monofilament braided" with --monofilament, braided--.
Claim 20, Column 20, Line 40; replace "ultrahigh" with --ultra-high--.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*